(12) United States Patent
Eidenschink et al.

(10) Patent No.: US 6,602,225 B2
(45) Date of Patent: Aug. 5, 2003

(54) SUBSTANTIALLY CIRCULAR CATHETER ASSEMBLY

(75) Inventors: Tracee Eidenschink, Wayzata, MN (US); Jason Lenz, Maplewood, MN (US)

(73) Assignee: SciMed Life Systems, Inc, Maple Grove, MN (US)

( * ) Notice: Subject to any disclaimer, the term of this patent is extended or adjusted under 35 U.S.C. 154(b) by 0 days.

(21) Appl. No.: 09/795,862

(22) Filed: Feb. 28, 2001

(65) Prior Publication Data

US 2002/0120233 A1 Aug. 29, 2002

(51) Int. Cl.[7] ............................................. A61M 29/00
(52) U.S. Cl. .................. 604/101.01; 606/191; 606/194
(58) Field of Search ........................ 604/96.01, 101.01, 604/101.04, 915, 919; 606/191, 192, 194

(56) References Cited

U.S. PATENT DOCUMENTS

| | | | |
|---|---|---|---|
| 5,549,551 A | * | 8/1996 | Peacock et al. ......... 604/103.05 |
| 5,571,087 A | * | 11/1996 | Ressemann et al. ......... 604/264 |
| 5,669,924 A | * | 9/1997 | Shaknovich ............ 604/101.04 |
| 5,921,958 A | * | 7/1999 | Ressemann et al. ......... 604/269 |
| 6,039,749 A | * | 3/2000 | Marin et al. ............ 604/103.07 |
| 6,142,973 A | * | 11/2000 | Carleton et al. ............. 604/915 |

* cited by examiner

*Primary Examiner*—Edward K. Look
*Assistant Examiner*—John K Fristoe, Jr.
(74) *Attorney, Agent, or Firm*—Vidas, Arrett & Steinkraus P.A.

(57) ABSTRACT

A catheter assembly of the type having at least two balloon catheters extending from a proximal end of the assembly to a distal end of the assembly. At least a portion of the assembly having a cross-sectional profile having a cross-sectional profile which is substantially circular in shape.

13 Claims, 5 Drawing Sheets

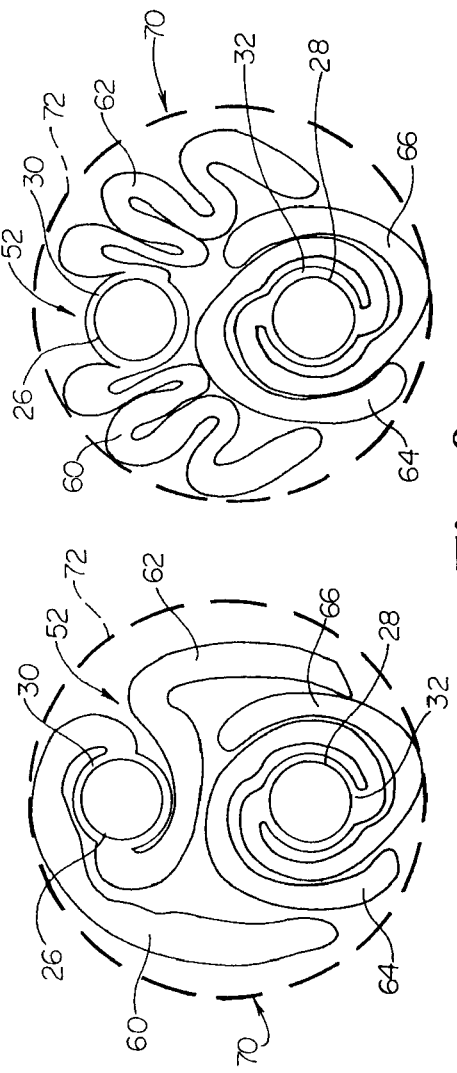
Fig. 6
Fig. 7
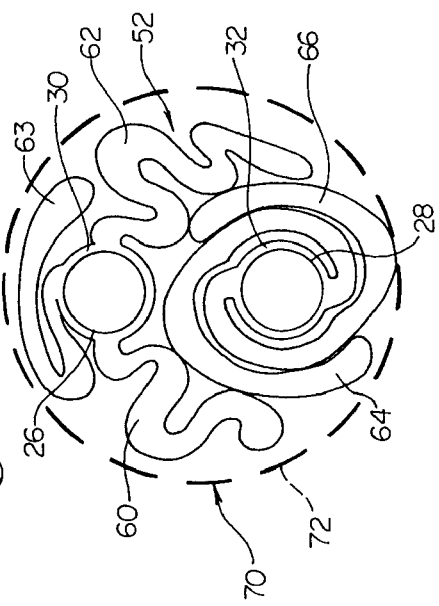
Fig. 8

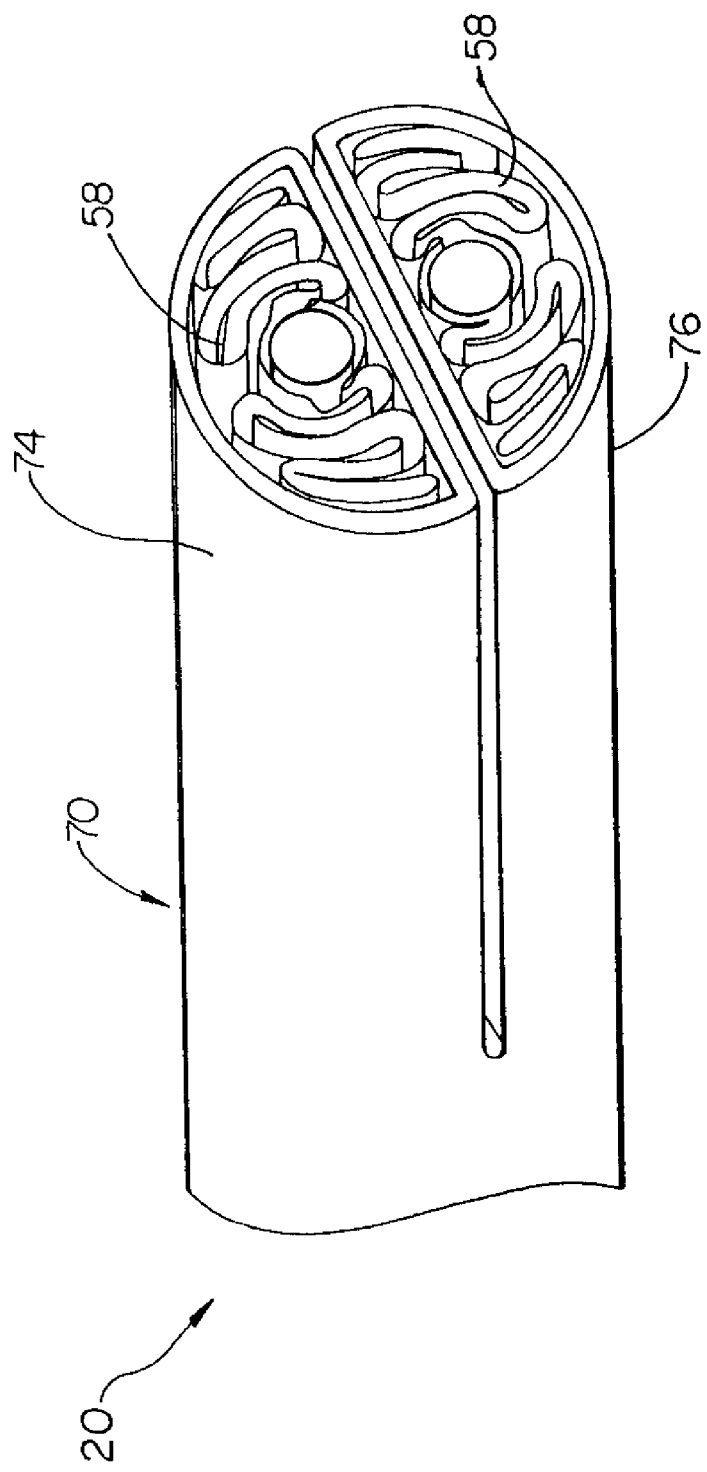

SUBSTANTIALLY CIRCULAR CATHETER ASSEMBLY

STATEMENT REGARDING FEDERALLY SPONSORED RESEARCH

Not Applicable

CROSS-REFERENCE TO RELATED APPLICATIONS

Not Applicable

BACKGROUND OF THE INVENTION

1. Field of the Invention

This invention relates to a catheter assembly having at least two balloon catheters which are mounted in a longitudinally overlapping manner in a guide catheter assembly. More specifically, the present invention is directed to a bifurcated stent delivery catheter and a method of preparing the same. The catheter of the present invention presents an improvement over known prior bifurcated stent delivery catheters, by providing a catheter assembly with a more circular cross-section than that of known prior bifurcated stent delivery systems.

2. Description of the Related Art

Percutaneous transluminal coronary angioplasty (PTCA) is a procedure which is well established for the treatment of blockages in the coronary arteries. Blockages may occur from cholesterol precipitation on the coronary wall which may be in any stage from initial deposit through aged lesions. Coronary arteries may also become blocked due to formation of thrombus.

The most widely used form of percutaneous coronary angioplasty makes use of a dilatation balloon catheter which is introduced into and advanced through a lumen or body vessel until the distal end thereof is at a desired location in the vasculature. Once in position across a lesion site, the expandable portion of the catheter, or balloon, is inflated to a predetermined size with a fluid at relatively high pressures, to radially compress the atherosclerotic plaque of the lesion against the inside of the artery wall and thereby dilate the lumen of the artery. The balloon is then deflated to a small profile so that the dilatation catheter may be withdrawn from the patients vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To reduce restenosis and strengthen the area, a physician can implant an intravascular prosthesis for maintaining vascular patency, such as a stent, inside the artery at the lesion.

Expandable, implantable medical devices such as stents are utilized in a number of medical procedures and situations as are stent delivery assemblies. As such, their structure and function are well known. A stent is a generally cylindrical prosthesis introduced via a catheter into a lumen of a body vessel in a configuration having a generally reduced diameter and then expanded to the diameter of the vessel. The stent may be self-expanding, such as a NITINOL shape memory stent, or it may be expandable by means of an inflatable portion of the catheter, such as a balloon. In its expanded configuration, the stent supports and reinforces the vessel walls while maintaining the vessel in an open, unobstructed condition.

Some stents have been developed specifically to address the problems that arise in the treatment of stenoses at or near the site of a bifurcation of a body lumen are known in the art. Further, single bifurcated stents and grafts have been developed in order to treat such conditions at the site of a branch of a body lumen. A bifurcated stent and/or graft typically comprises a tubular body or trunk and two tubular legs. Examples of bifurcated stents are shown in U.S. Pat. No. 5,723,004 to Dereume et al., U.S. Pat. No. 4,994,071 to MacGregor, and U.S. Pat. No. 5,755,735 to Richter, et al.

Various techniques have been used to deliver multiple prostheses in order to provide radial support to both a main blood vessel, and contemporaneously to side branches of the blood vessel. Examples of catheters for use in treating bifurcated lumens or delivery systems for bifurcated stents, are shown in U.S. Pat. No. 5,720,735 to Dorros, U.S. Pat. No. 5,669,924 to Shaknovich, U.S. Pat. No. 5,749,825 to Fischell, et al., U.S. Pat. No. 5,718,724 to Goicoechea et al., and U.S. Pat. No. 6,129,738 to Lashinski et al. As maybe seen from these references, in most bifurcated stent delivery systems, the bifurcated stent is mounted on a catheter assembly which comprises essentially two balloon catheters mounted in a guide catheter assembly.

In advancing a catheter equipped with an inflation expandable stent, particularly a bifurcated stent, through a body vessel to the deployment site, there are a number of important considerations. Of particular importance to the present invention is the shape and size of the cross-sectional "profile" of the catheter and stent. The profile of a catheter is the outer diameter (OD) of the catheter and the associated stent, as well as, the shape of the catheter's cross-section.

One way in which a catheter may be provided with a reduced profile is by providing the balloon portion of the catheter with a folded arrangement which provides an overall reduction in diameter in at least one axis. Many balloon folding configurations are know. For example, U.S. Pat. No. 5,792,172 to Fischell et al., U.S. Pat. No. 6,033,380 to Butaric et al., and U.S. Pat. No. 5,746,745 to Abele et al. each describe various methods of folding the balloon of a balloon catheter.

In addition to providing a balloon catheter with a reduced diameter, a catheter assembly having a profile which is round or substantially circular in cross-section is also desirable, as the round shape largely corresponds to the shape of the various vessels through which the assembly is advanced. A substantially circular assembly may be easier to manipulate within the body as the shape of the assembly is less likely to interfere with or be interfered by the vessel walls.

In most cases, an individual catheter regardless of the OD, may have a profile which is substantially circular in shape throughout the length of the catheter. In the case of a catheter assembly for use in treating a bifurcated lumen however, such "bifurcated catheters" may in fact employ two individual balloon catheters stacked upon one another within a guide catheter assembly. Such a stacked configuration of circular catheters will result in a catheter assembly having an ellipsoid or oval shaped cross-sectional profile, such as is depicted in prior art FIG. 1.

It is also known that typical balloon catheters employ inflatable portions or balloons which have wrapping configurations to provide the balloon with a round profile. As may be seen in FIG. 1, the resulting stacked balloons of the two balloon catheters will also have the undesirable oval shaped profile.

The oval shape of prior bifurcated catheters and/or stent delivery systems affects the ease and ability of the dilatation catheter to pass through a guide catheter, the coronary arteries, and across a lesion. In addition, such non-round shapes may be prone to interfere with and even damage vessel walls as the assembly is advanced through and manipulated therein.

In order to prevent potential harm to the vasculature and to provide a bifurcated stent delivery system which is more easily manipulated and used, the present invention provides for a catheter assembly for use in the treatment of a bifurcated lumen wherein at least a portion of the assembly has a more rounded cross-sectional profile than assemblies previously available.

All US patents, applications and all other published documents mentioned anywhere in this application are incorporated herein by reference in their entirety.

BRIEF SUMMARY OF THE INVENTION

This invention provides for a bifurcated catheter assembly wherein at least a portion of the assembly has a substantially circular cross-sectional profile.

The present invention is directed to a catheter assembly for treatment of a bifurcated lumen. The assembly has a proximal end and a distal end with a pair of balloon catheters extending therebetween. Each of the balloon catheters employs a shaft and an inflatable portion. At least a portion of the assembly having a circular cross-section.

By providing a circular cross-section to at least a portion of the assembly, the assembly may be more easily manipulated and advanced through the vasculature of the body. In addition, where a portion of the distal end of the assembly is provided with a substantially circular cross-section, the assembly may be made to be more readily inserted into a similarly shaped vessel or lumen, than previous assemblies having ellipsoid or oval shaped profiles.

In at least one embodiment of the invention, each of the shafts of the individual balloon catheters has a shape which when held in adjacent proximity to one another provides the shaft portion of the assembly with a substantially circular cross-section.

In at least one embodiment of the invention, at least a portion of each of the shafts is provided with an oval or D-shaped profile.

In at least one embodiment of the invention, the catheter assembly utilizes a novel method for folding and/or arranging the balloons of the individual catheters to provide an assembly which has a more round cross-sectional profile than previously known.

In at least one embodiment of the invention the inflatable portions or balloons of the balloon catheters may be folded in a complimentary configuration which provides for the desired substantially circular cross-sectional profile. The balloons may be folded in a variety of manners which provide at least a portion of the distal end of the assembly with the substantially circular cross-section.

In at least one embodiment of the invention the assembly may include a stent disposed about at least a portion of the inflatable portions of the catheters. The stent may be a standard tubular stent or it may be bifurcated.

BRIEF DESCRIPTION OF THE SEVERAL VIEWS OF THE DRAWINGS

A detailed description of the invention is hereafter described with specific reference being made to the drawings in which:

FIG. 6 is a cross-sectional view of a portion of an embodiment of the invention;

FIG. 7 is a cross-sectional view of a portion of an embodiment of the invention;

FIG. 8 is a cross-sectional view of a portion of an embodiment of the invention; and FIG. 9 is a perspective cross-sectional view of an embodiment of the invention.

DETAILED DESCRIPTION OF THE INVENTION

As mentioned above, it is well known that most lumens or vessels of the human body have a substantially circular cross-sectional profile. Where a medical device such as a catheter and/or a prosthesis is to be inserted into the vessel it would be beneficial to provide such devices with a shape and size which correspond to the vessel into which the device is to be inserted. Unfortunately, in the case of catheter assembles designed for the treatment of a bifurcated vessel, an example of which is illustrated in prior art FIG. 1, the assembly 10 typically will employ a pair of catheters 12 which when assembled together will have an oval or ellipsoid cross-sectional profile 14. While the OD of the assembly may be sufficiently small to allow the assembly to be inserted into an appropriately sized vessel, the oval shape of the assembly presents several problems such as have been described herein above.

Figure 2:
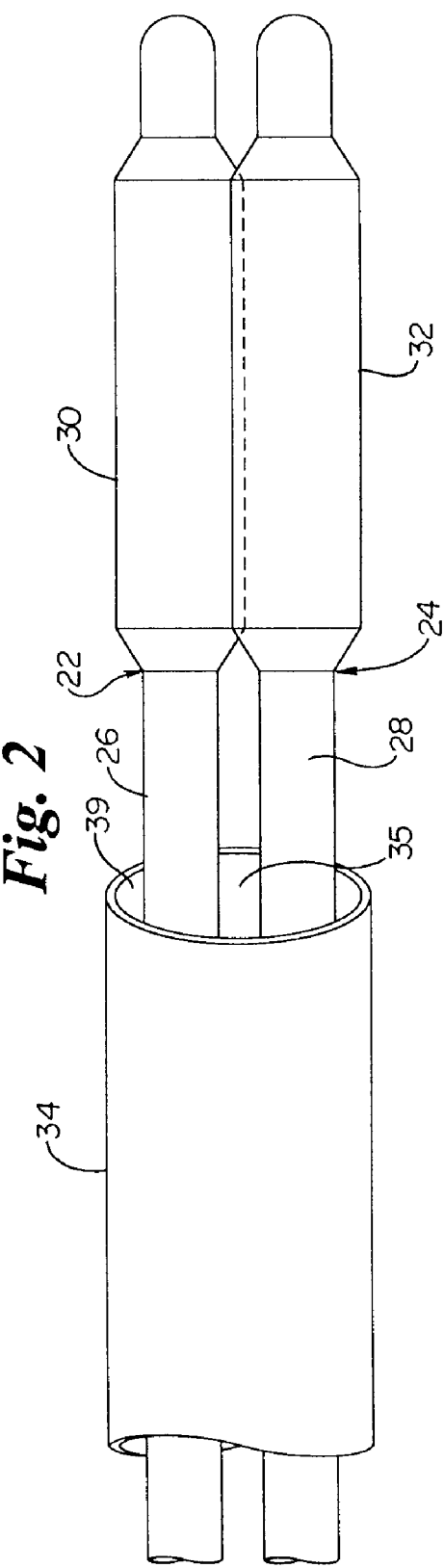
FIG. 2 is a perspective view of an embodiment of the invention.

The present invention avoids the use of an oval shaped catheter assembly by providing an assembly 20 of which at least a portion is substantially circular in cross-sectional profile, such as may be seen in FIG. 2.

In FIG. 2 an embodiment of the invention is shown which includes a catheter assembly, indicated generally at 20, which includes a pair of balloon catheters 22 and 24. Each balloon catheter includes a shaft 26 and 28, and an inflatable portion or balloon 30 and 32. At least a portion of the catheter 22 and 24 may be contained within a guide catheter 34 which keeps the catheter shafts 26 and 28 in close proximity to one another thereby providing the assembly 20 with a relatively compact profile. The guide catheter 34 may be configured to contain the catheters 22 and 24 in the substantially circular lumen 35 which is defined by the guide catheter housing 37.

The assembly 20 may be configured to have a cross-sectional profile throughout its entire length or a portion thereof. In the embodiment shown in FIG. 2, the guide catheter is disposed about the catheters 22 and 24 and provides the assembly with a substantially circular shape. However, due to the circular shape of the catheter shafts 22 and 24 a significant portion of the lumen 35 is wasted space 39. In alternative embodiments of the invention the catheters 22 and 24 and/or portions thereof may be uniquely configured to provide the desired substantially circular profile, rather than relying exclusively on the circular shape of the housing 37.

Figure 3:
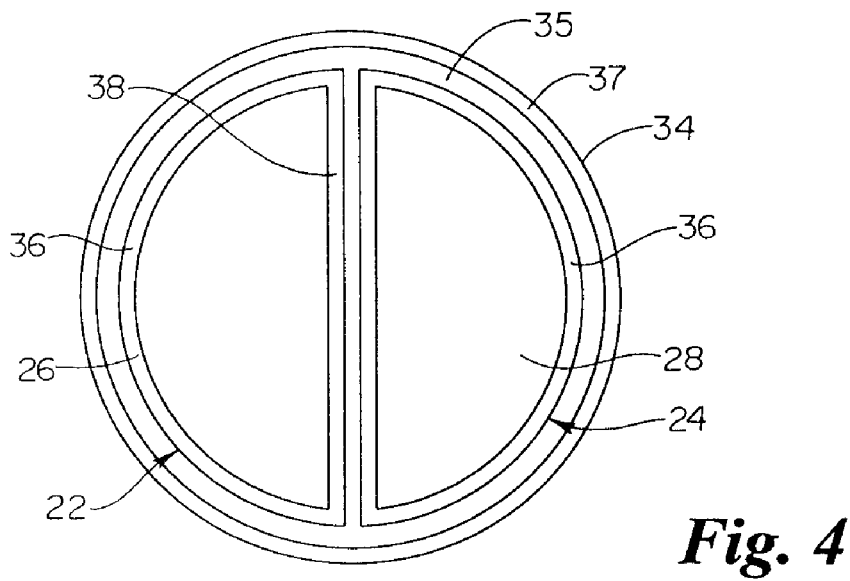
FIG. 3 is a cross-sectional view of a portion of an embodiment of the invention.

As may be seen in FIG. 3, the catheter shafts 26 and 28 may be provided with a D-shaped cross-section having a curved portion 36 and a relatively straight or flat portion 38. By abutting the flat portions 38 of each shaft 26 and 28, the unique shape of the shafts 26 and 28 allows them to collectively acquire the substantially circular shape depicted. When contained within the guide catheter 34, the portion of the assembly 20 corresponding to the catheter shafts 26 and 28 will be provided with a substantially circular cross-sectional profile.

Clearly, it may be seen that the D-shaped shafts 26 and 28, positioned in the manner shown, will provide the assembly 20 with the desired rounded profile however, alternative shapes and configurations may be utilized. As may be seen in FIG. 4, the shafts 26 and 28 are each provided with an oval shape. When arranged in the manner shown, where the shafts 26 and 28 are held adjacent to one another with the longer axis, indicated by line 40, of each shaft 26 and 28 being substantially parallel, the assembly may be provided with a substantially circular profile. Though the oval shaped catheter shafts 26 and 28 do not themselves provide the desired substantially circular profile, when contained within the guide catheter 34, the oval shaped shafts 26 and 28 provide sufficient structural support to the guide catheter 34, that the guide catheter 24 and thus the corresponding portion of the assembly 20 will be substantially circular in profile as shown.

Figure 4:
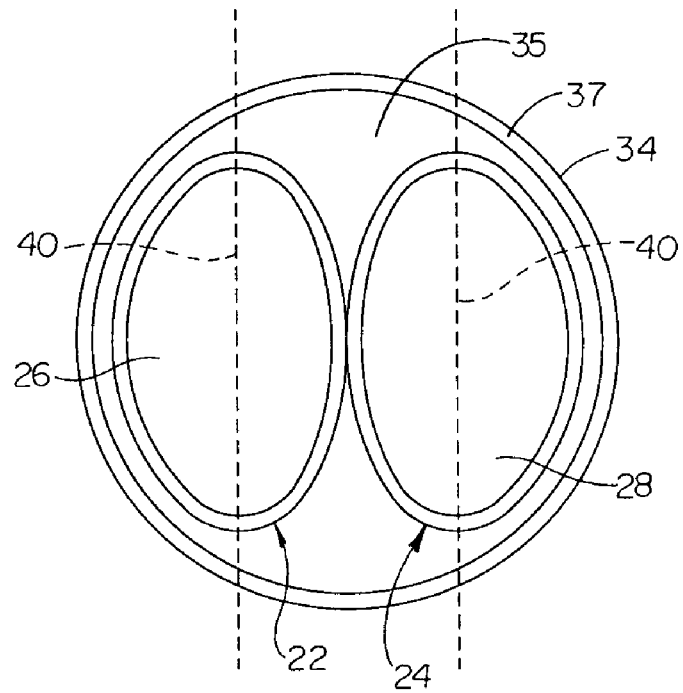
FIG. 4 is a perspective view of is a cross-sectional view of a portion of an embodiment of the invention.

While FIGS. 3 and 4 depict only two configurations of catheter shafts which may provide at least a portion of a two catheter assembly with a substantially circular cross section, the present invention is directed to all configurations which provide a two catheter or bifurcated catheter assembly with a substantially circular cross-sectional profile.

Figure 5:
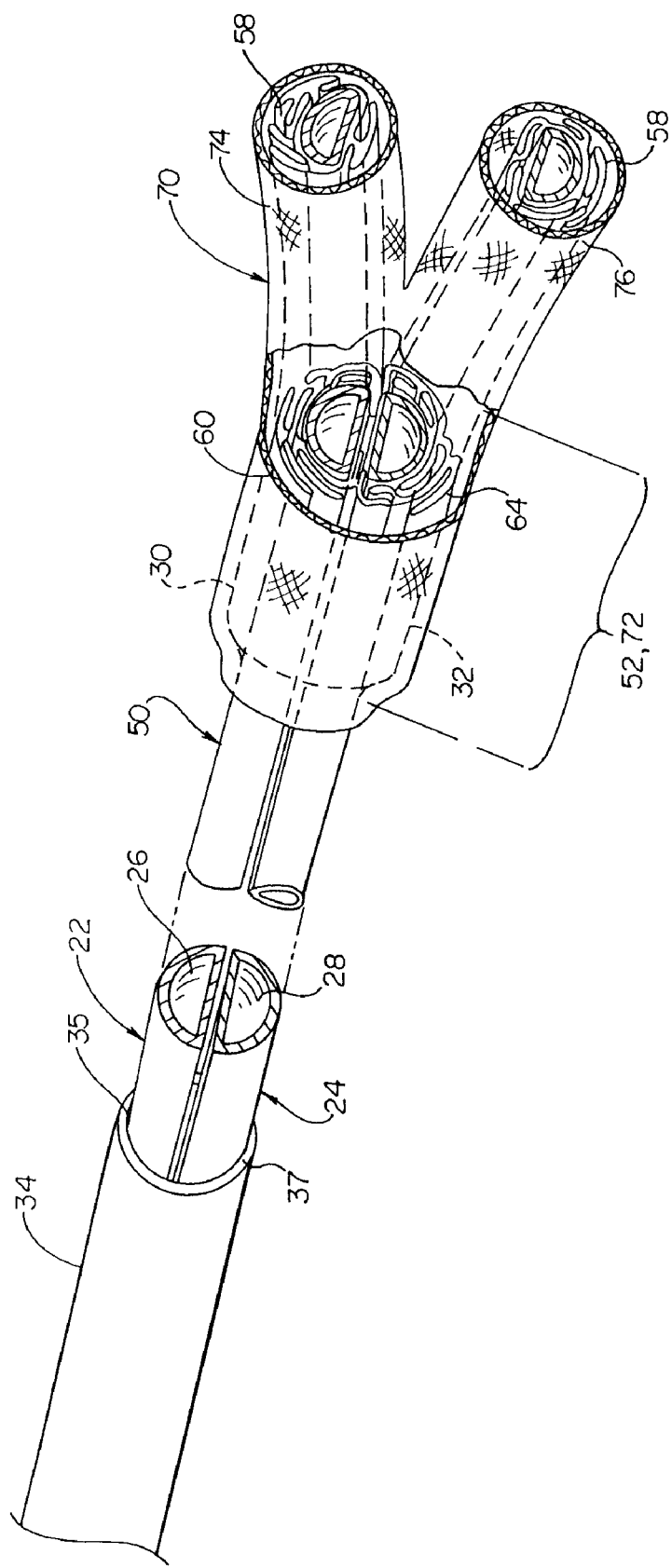
FIG. 5 is a partial cross-section and perspective view of an embodiment of the invention.

In addition to providing the portion of a catheter assembly 20 which corresponds to the placement of the shafts 26 and 28 of the individual balloon catheters 22 and 24, the present invention is also directed to providing at least a portion of the distal end 50 of an assembly 20 with a substantially circular cross-sectional profile such as may be seen in FIG. 5.

Figure 1:
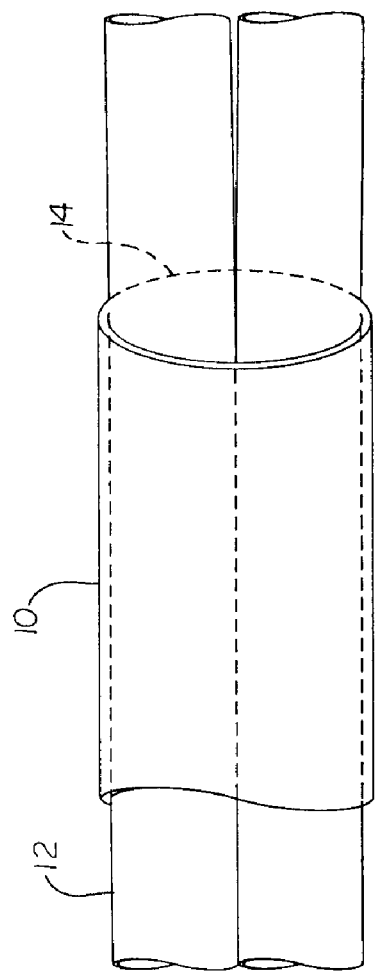
FIG. 1 is a perspective view of a PRIOR ART bifurcated catheter.

In FIG. 5, a portion of the distal end 50 of a bifurcated catheter assembly 20 is shown. At the distal end 50 of the assembly 20 the shafts 26 and 28 each respectively have a inflatable portion or balloon 30 and 32 mounted thereon. In prior designs such as depicted in FIG. 1, the balloons are typically folded about the shaft to provide a compact profile. Typically, such individual balloon profiles are round resulting in an oval shaped profile such as may be seen in FIG. 1. In the present invention, shown in FIG. 5 the balloons 30 and 32 may be folded and positioned in such a manner so as to provide the assembly with the desired substantially circular shaped profile.

In the embodiment shown in FIG. 5, the balloons 30 and 32 are shown prior to deployment. In this configuration the balloons 30 and 32 or at least a portion of each may be held substantially parallel and immediately adjacent to one another. The portion of the distal end 50 where the balloons 30 and 32 are immediately adjacent to one another may be characterized as a common portion 52 of the distal end 50. In the common portion 52 the balloons 30 and 32 may be provided with folded configurations which provide the common portion 52 with a substantially circular profile such as is shown.

While various balloon folding configurations may be utilized to provide the distal end 50 or at least the common portion 52 with the rounded shape desired, three examples of balloon folding techniques are provided herein.

In the embodiment shown in FIG. 6 the first balloon 30 is provided with a pair of wings 60 and 62 which are wrapped partially around the shaft 26 and then extend partially around the second balloon 32. As may be seen, the second balloon 32 may have wings 64 and 66 which wrapped in a mutual spiral about the second catheter shaft 28. The wings 60 and 62 of the first balloon 30 may be partially wrapped respectively over the wings 64 and 66 of the second balloon 32.

In the embodiment shown in FIG. 7, the second balloon 32 has the same mutually wrapped configuration of wings 64 and 66 as shown in FIG. 6. However, the folds 60 and 62 of the first balloon 30 each comprise an undulating or "zig-zag" shape. The wings 60 and 62 respectively extend out to rest upon or contact a wing 64 and 66 of the second balloon 32 in the manner shown.

In yet another configuration shown in FIG. 8, the first balloon is equipped with a third balloon fold 63 which is folded atop the shaft 26. The remaining folds 60 and 62 are draped over the second balloon 32 in the manner shown.

In the various embodiments depicted in FIGS. 6–8, the shafts 26 and 28 may have individual profiles which are round, D-shaped, oval or any other configuration desired.

In the various embodiments depicted in FIGS. 5–8, the assembly 20 may be seen to include a bifurcated stent 70 such as has been previously described. As may be seen in FIG. 5, the stent 70 also includes a common portion 72 which may be disposed over a portion of both of the balloons 30 and 32, such as may be seen in FIGS. 6–8. Where the balloons diverged from the common area 52, such as is shown in FIG. 5, the stent may include one or more arms such as 74 and 76 which are disposed over the distal portions 58 of each balloon 30 and 32.

In addition, the distal portions 58 of the balloons 30 and 32 may also be provided with a substantially-circular cross section even when carrying a stent 70. Turning to FIG. 9, an embodiment of the invention is shown where the arms 74 and 76 of the stent 70 are each provided with a D-shaped profile, similar to the D-shaped profile of the catheter shafts depicted in FIG. 3 and described above. Where the stent is equipped with such D-shaped arms 74 and 76, the balloons 30 and 32 may be respectively folded in such a manner as to provide a the distal portions 58 of each balloon 30 and 32 with a D-shaped or hemispherical profile such is shown in FIG. 9.

It should be noted where a stent 70, such as depicted in FIG. 9, is employed with the catheter assembly 20, the arms 74 and 76 of the stent as well as the balloons 30 and 32 may be constructed such that in the unexpanded state they have the D-shaped profile shown, but when expanded they may be substantially round or circular in profile. In such an embodiment the balloons 30 and 32 are configured to have a round profile when in the inflated state. The force exerted by the expanded balloons on the stent arms 74 and 76 will cause the arms 74 and 76 to assume the shape of the respective balloons 30 and 32.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A catheter assembly for treatment of a bifurcated lumen, the assembly having a proximal end and a distal end, the assembly comprising:

a first balloon catheter having a first catheter shaft and a first balloon mounted thereon, at least a portion of the first catheter shaft being substantially D-shaped in cross-section; and a second balloon catheter having a second catheter shaft and a second balloon mounted thereon, at least a portion of the second catheter shaft being substantially D-shaped in cross-section, the first and second balloon catheters extending from the proximal end to the distal end of the assembly, the first balloon and the second balloon being positioned at the distal end of the assembly, at least a portion of the assembly having a substantially circular cross-section.

2. The catheter assembly of claim 1 further comprising a housing, the housing being disposed about at least a portion of the first balloon catheter and at least a portion of the second balloon catheter, the at least a portion of the first balloon catheter and the at least a portion of the second balloon catheter being positioned substantially parallel to one another.

3. The catheter assembly of claim 1 wherein the at least a portion of the assembly comprises at least a portion of the first catheter shaft and at least a portion of the second catheter shaft.

4. The catheter assembly of claim 1 wherein the first catheter shaft has a first curved portion and a first flat portion and the second catheter shaft has a second curved portion and a second flat portion, the first flat portion being positioned immediately adjacent to the second flat portion.

5. The catheter assembly of claim 2 wherein at least a portion of the first balloon and the at least a portion of the second balloon substantially parallel to one another.

6. The catheter assembly of claim 5 further comprising a bifurcated stent, the bifurcated stent having a first arm region, a second arm region and a common region, the first arm region being disposed about a distal portion of the first balloon, the second arm region being disposed about a distal portion of the second balloon, the common region being disposed about the at least a portion of the first balloon and the at least a portion of the second balloon which are substantially parallel, at least a portion of the common region having a substantially circular cross-sectional profile.

7. The catheter assembly of claim 5 wherein the first balloon and the second balloon are each folded in a predetermined manner so as to provide the circular cross-section of the at least a portion of the distal end of the assembly.

8. The catheter assembly of claim 7 wherein the first balloon has at least two balloon folds and the second balloon has at least two balloon folds.

9. The catheter assembly of claim 7 wherein at least a portion of each of the at least two balloon folds of the first balloon at least partially overlap at least a portion of each of the at least two balloon folds of the second balloon.

10. The catheter assembly of claim 8 wherein each of the at least two balloon folds of the first balloon are folded in an undulating configuration.

11. The catheter assembly of claim 7 wherein the first balloon has at least three folds and the second balloon has at least two folds.

12. The catheter assembly of claim 6 wherein the first arm region and the second arm region each have a substantially D-shaped profile.

13. The catheter assembly of claim 12 where in the first arm region has a first curved portion and a first flat portion and the second arm region has a second curved portion and a second flat portion, the first flat portion being positioned immediately adjacent to the second flat portion.

* * * * *